US00PP18546P3

(12) United States Plant Patent
Ault

(10) Patent No.: US PP18,546 P3
(45) Date of Patent: Mar. 4, 2008

(54) ***ECHINACEA* PLANT NAMED 'CBG CONE 2'**

(50) Latin Name: ***Echinacea* hybrid**
Varietal Denomination: CBG Cone 2

(75) Inventor: James R. Ault, Libertyville, IL (US)

(73) Assignee: Chicagoland Grows, Inc., Glencoe, IL (US)

( * ) Notice: Subject to any disclaimer, the term of this patent is extended or adjusted under 35 U.S.C. 154(b) by 4 days.

(21) Appl. No.: 11/527,185

(22) Filed: Sep. 26, 2006

(65) Prior Publication Data

US 2007/0240245 P1 Oct. 11, 2007

(51) Int. Cl.
*A01H 5/00* (2006.01)

(52) U.S. Cl. ..... Plt./263
(58) Field of Classification Search ..... Plt./258, Plt./263
See application file for complete search history.

(56) References Cited

U.S. PATENT DOCUMENTS

PP12,242 P2 * 12/2001 Hawks ..... Plt./263

OTHER PUBLICATIONS

UPOV ROM GTITM Database, GTI JOUVE Retrieval Software 2007/01 Citation For 'CBG cone2'.*

* cited by examiner

*Primary Examiner*—Wendy Haas
(74) *Attorney, Agent, or Firm*—Penny J. Aguirre

(57) ABSTRACT

A new cultivar of hybrid *Echinacea,* 'CBG Cone 2', characterized by its compact and dwarf growth habit, its sturdy stems, its horizontally held blooms with medium pink florets surrounding yellow-brown cones, its long blooming habit, its ease of propagation, its vigorous growth habit, and its hardiness in U.S.D.A. Zones 4 to 9.

2 Drawing Sheets

Botanical classification: *Echinacea* hybrid.
Variety denomination: 'CBG Cone 2'.

BACKGROUND OF THE INVENTION

The present invention relates to a new and distinct cultivar of hybrid *Echinacea* and will be referred to hereafter by its cultivar name, 'CBG Cone 2'. 'CBG Cone 2' represents a new purple coneflower, an herbaceous perennial grown for landscape use.

The new cultivar, 'CBG Cone 2', is a selection that arose from an on going breeding program conducted by the inventor in Glencoe, Ill. with the goal of developing new cultivars of *Echinacea* with desirable garden performance combined with attractive foliage and flowers. 'CBG Cone 2' arose from a controlled cross between unnamed plants of the female parent *Echinacea tennesseensis×purpurea* and the male parent *Echinacea angustifolia×tennesseesis*. 'CBG Cone 2' was selected as unique in July of 2002 for its compact dwarf habit, its dense foliage held on strong stems and for its long blooming habit with blooms that have medium pink ray florets surrounding yellow-brown cones.

Asexual reproduction of the new cultivar was first accomplished by division in June of 2003 followed by in vitro propagation in 2004 by the inventor in Glencoe, Ill. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'CBG Cone 2' as a unique cultivar of *Echinacea*.

1. 'CBG Cone 2' exhibits sturdy, well-branched stems and dense foliage resulting in a compact growth habit.
2. 'CBG Cone 2' exhibits a dwarf plant habit, reaching a height of 45 to 50 cm (18 to 20 inches).
3. 'CBG Cone 2' is long blooming, blooming heavily from mid July to mid August with a few blooms remaining in color in September.
4. 'CBG Cone 2' exhibits well formed, horizontally held blooms with ray florets that are medium pink in color surrounding yellow-brown colored cones.
5. 'CBG Cone 2' is readily propagated by tissue culture and has a vigorous grower.
6. 'CBG Cone 2' is reliably hardy in U.S.D.A. Zones 4 to 9.

The new *Echinacea* is unique in comparison to other cultivars and species of *Echinacea* known to the inventor. The cultivar, *Echinacea* 'Kim's Knee High' (U.S. Plant Pat. No. 12,242) is similar in that it has a dwarf plant habit, however 'Kim's Knee High' differs in having blooms that have ray florets that are pinkish red in color and cones that are reddish brown in color.

'CBG Cone 2' can be compared to the species of its parent hybrids. 'CBG Cone 2' differs from *Echinacea purpurea* in having shorter stems, more basal branching, basal foliage that is more linear in shape and more pubescent, and ray florets that are shorter and held consistently horizontal, c differs from *Echinacea tennesseensis* in having more pubescent stems and leaves, and ray florets that are held horizontal; the ray florets of *E. tennesseensis* are curved upwards at a 90° angle from horizontal.

BRIEF DESCRIPTION OF THE DRAWINGS

The plants and plant parts in the photographs depict six month-old plants of 'CBG Cone 2' as field grown from 32-cell tissue culture planetlets in St. Charles, Ill.

Figure 1:
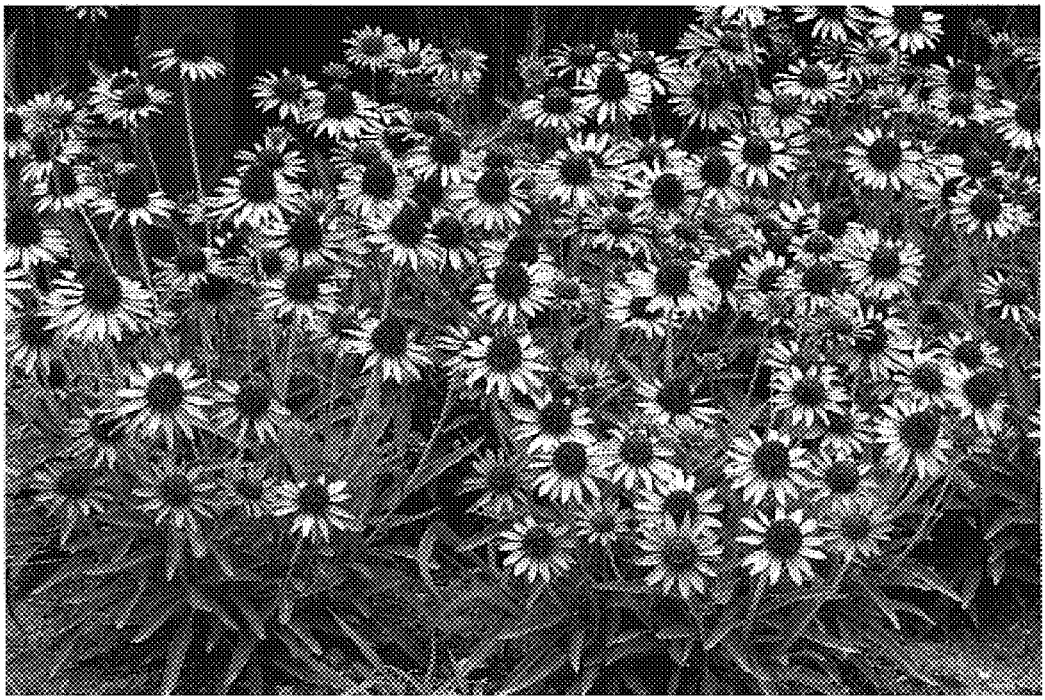
FIG. 1 depicts the plant habit when in peak bloom.
Figure 2:
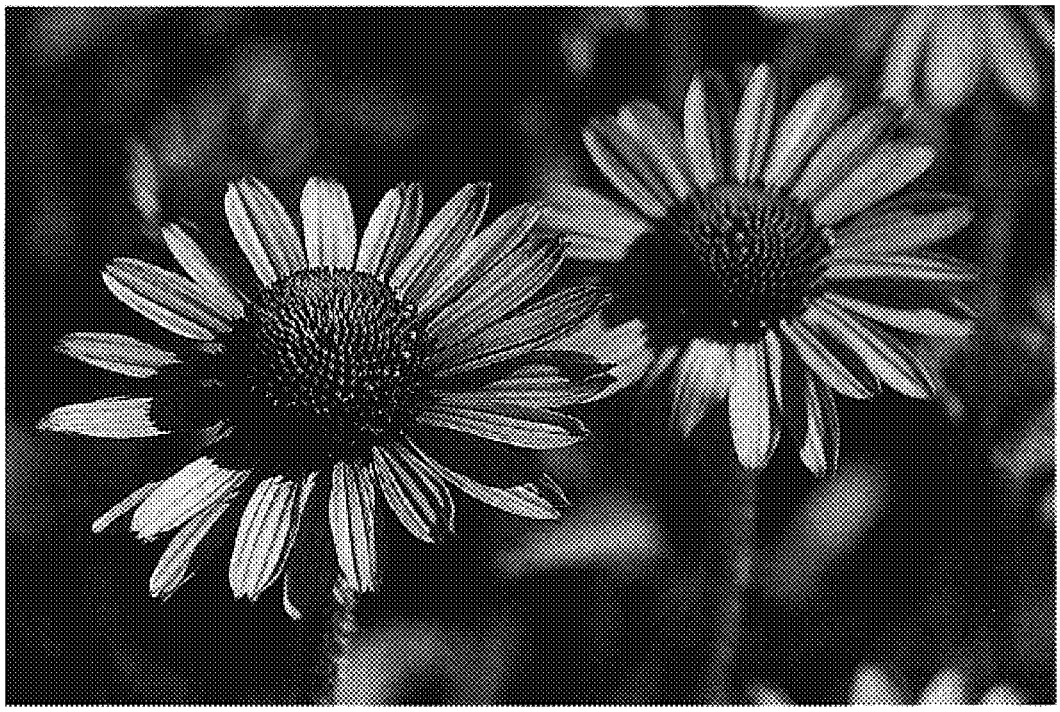
FIG. 2 shows a close-up of the blooms and FIG. 3 is a photograph of a trial plot with numerous plants.
Figure 3:
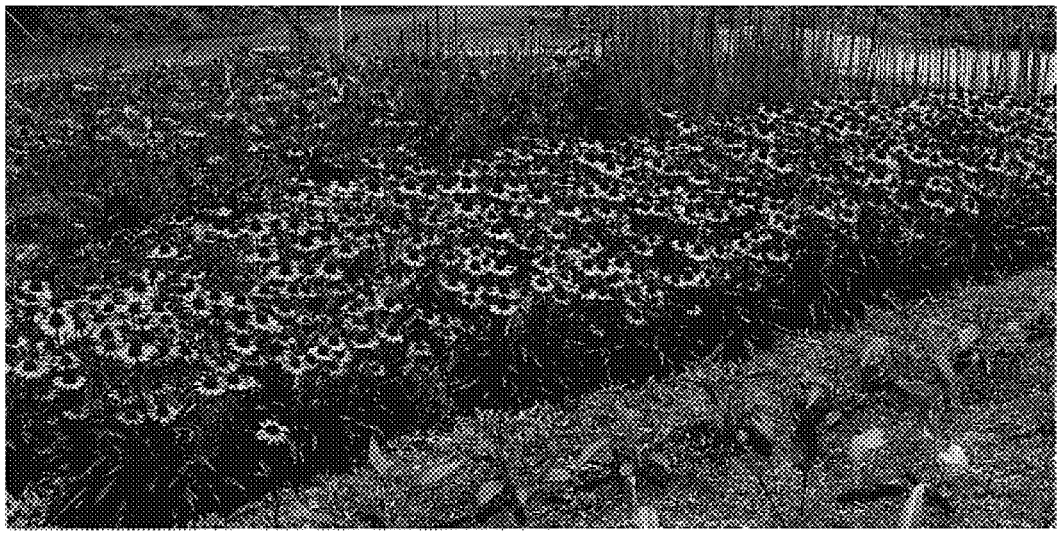

The colors in the photographs are as close as possible with the photographic and printing technology utilized. The color values cited in the detailed botanical description more accurately describe the colors of the new *Echinacea*.

BOTANICAL DESCRIPTION OF THE PLANT

The following is a detailed description of a six-month old plants the new cultivar as field grown from 32-cell tissue culture plantlets in Glencoe, Ill. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

Botanical classification: 'CBG Cone 2' is a cultivar of *Echinacea* of hybrid origin.

Parentage: Unnamed plants of the female parent *Echinacea tennesseensis×purpurea* and the male parent *Echinacea angustifolia×tennesseensis.*

General description:

*Blooming period.*—Blooming heavily from mid July to mid August with a few blooms remaining in color in September.

*Plant type.*—Herbaceous perennial.

*Plant habit.*—Dwarf, compact, clump-forming, upright.

*Height and spread.*—Up to 45 cm in height about 61 cm in width in 2 years of growth.

*Hardiness.*—U.S.D.A. Zones 4–9.

*Culture.*—Tolerant to a wide range of growing conditions, growing well in full sun to light shade, tolerant to drought.

*Diseases and Pests.*—No susceptibility or resistance to diseases or pests has been observed.

*Root description.*—Dark fibrous roots on short rhizomes.

*Growth rate.*—Vigorous.

*Propagation.*—Division and tissue culture.

Stem description:

*Shape.*—Slightly oval, solid.

*Stem color.*—145A with some areas suffused with 178B.

*Stem size.*—Ranges from about 3 to 5 mm in diameter and reaches about 40 cm in height including peduncle.

*Stem surface.*—Pubescent with fire white hairs about 1.5 mm in length becoming more numerous towards apex.

*Stem number.*—About 12 per one-gallon sized plant.

*Internode length.*—Typically 2.0 to 4.5 cm in length.

*Branching.*—Multiple basal branches.

Foliage description:

*Leaf shape.*—Lanceolate.

*Leaf division.*—Simple.

*Leaf base.*—Cuneate to long leaf-like petiole.

*Leaf apex.*—Acuminate.

*Leaf venation.*—Tri-nerved, upper surface 145B in color, lower surface mid rib is prominent and 145C in color, other veins on lower surface 145B.

*Leaf margins.*—Entire and ciliate.

*Leaf attachment.*—Petiolate.

*Leaf arrangement.*—Alternate.

*Leaf size.*—Up to 13 cm in length and 3.5 cm in width,

*Leaf color.*—Newly formed and mature, upper and lower surface; 137B to 137C.

*Leaf surface.*—Upper and lower slightly pubescent with fine hairs, rough, almost leathery.

*Petioles.*—Extended from leaf blade, range from 2 cm to 7 cm in length, typically about 2 mm in width at leaf blade and about 6 cm in width at stem, reflexed on upper surface, 145C in color with shadings of N77B, particularly on base of upper surface.

Flower description:

*Type.*—Capitulum, heterogamous with ray florets around the head margin and disk florets in the center, forming a radiant head.

*Capitulum number.*—One terminal capitulum per stem.

*Lastingness of inflorescence.*—About 4 to 6 weeks until senescence of ray flowers, disk flowers are persistent, a cut flower will last about 2 weeks.

*Capitulum size.*—Matures to about 2 cm in depth and 7 cm in diameter, disk size is about 1.5 cm in depth and 2.5 cm in diameter.

*Fragrance.*—None detected.

*Phyllaries.*—About 30 arranged in 3 overlapping rows, up to 2 cm in length and 5 mm in width, fused at base, acute apex, broadly lanceolate in shape, 137B to 137C in color, entire ciliate margin and glabrous hairy surface.

*Buds.*—Cup-shaped, up to 1.5 cm in diameter, phyllary are 137B to 137C in color and and disk flowers appear 138B in color when viewed in mass just prior to opening.

*Peduncle.*—Strong, sometimes curved, continuous with stem, typically 7 to 9 cm in length and 3 to 4 mm in diameter widening to about 5 mm at base of capitulum, 145A in color, texture is glabrous and rough with white hairs.

*Ray florets* (*sterile*).—13 to 17, oblong in shape, held nearly horizontal, vertical ridges on both surfaces, about 2.5 cm in length and 7 mm in width, emarginated apex, truncate base, entire margin except apex, glabrous in texture, initially held upright about 70° from horizontal and become horizontal as they mature, color of upper and lower surface when opening; 155A with an overlay of 62B with very end of tips N77A, color of upper surface when mature; blend of 68A to 68B with touch of 155B towards apex and N77A at very tips of apex, color of lower surface when mature; blend of 68B and 68C with touch of 155B especially towards apex and N77A at very tips of apex.

*Disk flowers* (*bisexual*).—Numerous, about 200, tubular in shape, arranged spirally on a conical receptacle, about 8 mm in length and 2 mm in width, surrounded by a pale; 1 cm in length and 2 mm in width, lanceolate in shape with an apex that terminates in a spine, color is 144B to 144C with an a spiny apex of N77B, as the floret matures the spine exceeds the length of the floret and defines the color of the disk once the reproductive organs, changing from yellow green tipped in purple (144B to 144C with N77B) and becoming purple (N77B) as the disk florets mature.

Reproductive organs (present on disk florets only):

*Gynoecium.*—Pistil; 1, 6 mm in length and 4 mm in width, style; 0.3 mm in width and 4 mm in length, color 155A becoming N77B towards apex, surrounded by stamens, stigma; bifid, each arm is reflexed, about 2.5 mm in length and N77B in color, Ovary; inferior, single-celled, 0.4 mm in diameter, 155A in color.

*Androcoecium.*—Stamens; 5, fused, form a cylinder around style, 5 mm in length and 0.7 mm in width, dehisced longitudinally, 200A in color filaments; 1.5 mm in length, 0.5 m in width, 155C in color, pollen; abundant and 13A in color.

*Fruit.*—Not observed, *Echinacea* is self-incompatible, fruit and seed would likely set if grown amongst other *Echinacea.*

I claim:

1. A new and distinct cultivar of *Echinacea* plant named 'CBG Cone 2' substantially as herein illustrated and described.

* * * * *